United States Patent [19]
Derleth et al.

[11] Patent Number: 5,527,754
[45] Date of Patent: Jun. 18, 1996

[54] CATALYTIC COMPOSITION AND PROCESS FOR THE OXYCHLORINATION OF ETHYLENE USING SUCH A COMPOSITION

[75] Inventors: Helmut Derleth, Nienburg; Deniz Adem, Binche; Michel Strebelle, Brussels, all of Belgium

[73] Assignee: Solvay (Société Anonyme), Brussels, Belgium

[21] Appl. No.: 350,994

[22] Filed: Nov. 29, 1994

[30] Foreign Application Priority Data

Dec. 8, 1993 [BE] Belgium .............................. 09301354

[51] Int. Cl.⁶ .......................... B01J 23/04; C07C 17/156
[52] U.S. Cl. .......................... 502/225; 502/224; 502/226; 502/340; 570/243; 570/245
[58] Field of Search ..................... 502/224, 225, 502/226, 340; 570/243, 245

[56] References Cited

U.S. PATENT DOCUMENTS

| | | | |
|---|---|---|---|
| 3,867,469 | 2/1975 | Ricks | 260/659 A |
| 4,124,534 | 11/1978 | Leitert et al. | 252/441 |
| 4,130,595 | 12/1978 | Bellis | 260/654 R |
| 4,753,914 | 6/1988 | Eichhorn et al. | 502/225 |
| 5,070,062 | 12/1991 | Canavesi et al. | 502/226 |

*Primary Examiner*—Sharon Gibson
*Attorney, Agent, or Firm*—Spencer & Frank

[57] ABSTRACT

Catalytic composition comprising copper chloride, magnesium chloride and caesium chloride deposited on an alumina, which may be used in particular for the oxychlorination of ethylene into 1,2-dichloroethane. In the processes for the oxychlorination of ethylene in oxygen in a fluid bed, this catalytic composition makes it possible to obtain an excellent yield of 1,2-dichloroethane without causing the deposition of soiling material on the surface of the bundle of tubes of the heat exchanger located in the reactor.

12 Claims, 1 Drawing Sheet

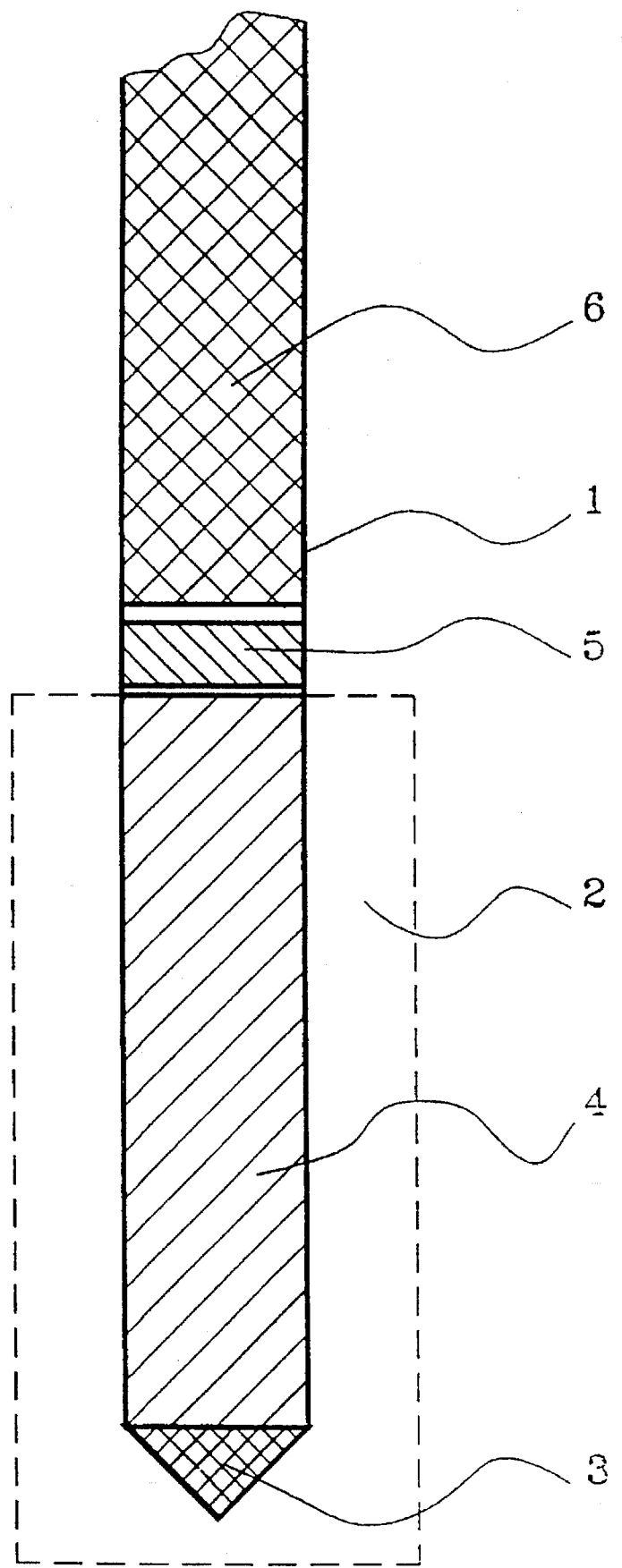

CATALYTIC COMPOSITION AND PROCESS FOR THE OXYCHLORINATION OF ETHYLENE USING SUCH A COMPOSITION

FIELD OF THE INVENTION

The present invention relates to a catalytic composition which may be used in oxychlorination and to a process for the oxychlorination of ethylene using such a catalytic composition.

TECHNOLOGY REVIEW

Oxychlorination, that is to say the chlorination of hydrocarbons by hydrogen chloride in the presence of air or of oxygen, constitutes a reaction which has been known for a long time and is usually carried out in the presence of catalysts consisting of metal salts deposited on inert supports such as aluminas, silica gels, mixed oxides or alternatively clays or other supports of natural origin. Industrially, the catalyst is most often used in a fluid bed but it may also be used in a fixed bed. The metal salts most often used are halides such as copper chloride. However, when used alone, copper chloride has the drawback of being relatively volatile, which results in a fall in catalytic activity and in the yield of the oxychlorination reaction, which is unacceptable in industrial plants.

It is well known to enhance the performance of oxychlorination catalysts consisting of supported copper chloride by addition of alkali metal chlorides, alkaline-earth metal chlorides or chlorides of rare-earth metals (lanthanides). In particular, catalytic compositions for oxychlorination which simultaneously comprise chlorides of copper, of magnesium and of alkali metals on alumina have already been proposed.

Application EP-A-0,255,156 from SOLVAY describes ternary catalytic compositions containing a mixture of chlorides of copper, of magnesium and of an alkali metal chosen from sodium or lithium, which are used in specific proportions and which enable a very good yield of 1,2-dichloroethane to be achieved in a fluid bed process for the oxychlorination of ethylene, while simultaneously reducing the corrosion of the stainless steel reactors by virtue especially of a reduction in the adhesion and lumping together of the catalyst particles.

Application EP-A-0,375,202 envisages ternary catalytic compositions based on copper chloride, magnesium chloride and potassium chloride, containing 30 to 90 g of copper, from 2 to 30 g of magnesium and from 2 to 30 g of potassium per kilo of catalytic composition, with a Cu:Mg:K atomic ratio of 1:0.1–1.0:0.1–1.0.

It has, however, been observed that most of the compositions of the prior art simultaneously comprising copper chloride, magnesium chloride and alkali metal chlorides deposited on alumina cause, in fluidized-bed type reactors for the oxychlorination of ethylene, the deposition of soiling material on the surface of the tubes of the heat exchanger located in the fluid bed. This phenomenon has been observed in particular in processes involving oxygen, in which processes the oxygen is used either in pure form or in the form of an oxygen and nitrogen mixture which is richer in oxygen than air. This behavior of the catalytic compositions constitutes a considerable obstacle to their use. The reason for this is that an increasingly thick layer of soiling material gradually builds up on the surface of the tubes, resulting in a progressive deterioration of the heat transfer. In addition, this phenomenon may, in the long run, cause corrosion. It is consequently essential to stop the reactors regularly in order to clean the bundle of tubes of the heat exchanger.

One of the objects of the present invention is consequently to provide catalytic compositions of particularly high performance which enable, in a process for the oxychlorination of ethylene in a fluid bed, a high yield of 1,2-dichloroethane to be achieved without causing the deposition of soiling material on the surface of the tubes of the heat exchanger, especially in processes involving oxygen.

SUMMARY OF THE INVENTION

Consequently, the present invention relates to a catalytic composition comprising copper chloride, magnesium chloride and an alkali metal chloride deposited on an alumina, which may be used in oxychlorination, characterized in that the alkali metal is caesium.

It also relates to a process for the oxychlorination of ethylene into 1,2-dichloroethane characterized in that the oxychlorination reaction is catalysed by a catalytic composition according to the invention.

The catalytic composition according to the invention generally contains, expressed as metal, from 30 to 90 g of copper, from 10 to 30 g of magnesium and from 0.05 to 15 g, preferably from 0.1 to 10 g, of caesium per kilo of catalytic composition.

BRIEF DESCRIPTION OF THE DRAWING

The drawing illustrates a finger tube (1) extending into a fluid bed (2). The tube comprises four distinct regions including an interface (5) just above the fluid bed, a cylindrical surface (4) below the fluid bed and a cylindrical surface (6) above the interface, and a cone tip (3).

DETAILED DESCRIPTION OF THE INVENTION

It has now been observed, surprisingly, that catalytic compositions containing copper chloride, magnesium chloride and caesium chloride in the amounts specified do not cause deposition of soiling material on the surface of the bundle of tubes of the heat exchanger located in the fluid bed, which is observed with the compositions of the prior art, while at the same time making it possible to achieve, in the oxychlorination of ethylene into 1,2-dichloroethane, a selectivity for 1,2-dichloroethane relative to the ethylene converted, and a yield of 1,2-dichloroethane relative to the hydrogen chloride used, which are similar to, or even better than, those obtained with the compositions of the prior art.

The catalytic compositions according to the invention contain at least 30 g of copper per kilo of catalytic composition, preferably at least 40 g per kilo and, in a particularly preferred manner, at least 50 g per kilo. They contain not more than 90 g of copper per kilo of catalytic composition. Those containing not more than 80 g thereof per kilo appear to be advantageous. Those containing not more than 70 g thereof per kilo appear to be particularly advantageous.

The catalytic compositions according to the invention contain at least 10 g of magnesium per kilo of catalytic composition, preferably at least 12 g per kilo and, in a particularly preferred manner, at least 15 g per kilo. They contain not more than 30 g of magnesium per kilo of catalytic composition. Those containing not more than 25 g thereof per kilo appear to be advantageous. Those containing not more than 20 g thereof per kilo appear to be particularly advantageous.

The catalytic compositions according to the invention preferably contain at least 0.1 g of caesium per kilo of catalytic composition, in a particularly preferred manner at least 0.5 g per kilo and, in a most particularly preferred manner, at least 1 g per kilo. They preferably contain not more than 10 g of caesium per kilo of catalytic composition. Those containing not more than 9 g thereof per kilo appear to be advantageous. Those containing not more than 6 g thereof per kilo appear to be particularly advantageous.

Good results for the oxychlorination of ethylene have been obtained with catalytic compositions containing from 40 to 80 g of copper, from 12 to 25 g of magnesium and from 0.5 to 9 g of caesium per kilo of catalytic composition.

In the compositions according to the invention, the Mg/Cu atomic ratio is preferably at least 0.3 and, in a particularly preferred manner, at least 0.5. Advantageously, this ratio does not exceed 1.5. Very advantageously, it does not exceed 1.0.

The Cs/Cu atomic ratio is preferably at least 0.003 and, in a particularly preferred manner, at least 0.005. Advantageously, this ratio does not exceed 0.10. Very advantageously, it does not exceed 0.08.

Very good results for the oxychlorination of ethylene have been obtained with compositions having Cu:Mg:Cs atomic ratios of 1:0.5–1.0:0.005–0.05.

In one variant in accordance with the invention, the catalytic composition additionally contains potassium. In this variant, the catalytic composition contains from 0.05 to 15 g, preferably from 0.1 to 10 g, of potassium per kilo of catalytic composition.

When potassium is present in the catalytic composition, the K/Cu atomic ratio is preferably at least 0.01 and, in a particularly preferred manner, at least 0.025. Advantageously, this ratio does not exceed 0.30. Very advantageously, it does not exceed 0.25.

The compositions according to the invention consisting essentially of copper chloride, magnesium chloride and caesium chloride deposited on alumina are, however, preferred.

The alumina used as support in the catalytic compositions of the invention may be of any origin and may be obtained according to any known process; aluminas of eta or gamma type are usually used. Good results have been obtained with a gamma alumina. The alumina used in the catalytic compositions of the invention generally has a mean particle diameter of between 10 and 200 μm and preferably has a mean diameter of between 20 and 120 μm. Its specific surface, measured according to the B.E.T. method, is generally between 50 m$^2$/g and 250 m$^2$/g. Good results for the oxychlorination of ethylene have been obtained with an alumina having a specific surface of from 100 m$^2$/g to 210 m$^2$/g. Finally, the pore volume of the aluminas usually used is between 0.1 and 1 cm$^3$/g. The pore volume is preferably between 0.2 and 0.8 cm$^3$/g and good results for the oxychlorination of ethylene have been obtained with an alumina having a pore volume of 0.3 to 0.6 cm$^3$/g.

The way in which the catalytic compositions according to the invention are produced is not critical. The metal chlorides may be introduced into the catalytic composition either directly in the form of chlorides, for example by impregnating the support using a solution containing a mixture of these salts, or in the form of other compounds of the metals, such as the oxides, the hydroxides, the nitrates or any other compound which is capable of being converted into chloride under the conditions in which the oxychlorination reactions are carried out. The preparation of the catalytic compositions may especially be performed in a rotating drum or in a fluidized bed, by impregnation of the alumina with a solution of the metal chlorides, in one or in several passes, and in the presence or absence of additives such as acids, for example hydrochloric acid.

One production method which has given good results consists in impregnating an alumina with an aqueous solution containing the appropriate amounts of copper chloride, magnesium chloride and caesium chloride, in which method the appearance of a liquid phase which is not absorbed by the solid is avoided by limiting the volume of the impregnating solution to 70 to 100% of the pore volume of the quantity of alumina used. The impregnated alumina is then dried before being introduced into the actual oxychlorination reactor.

The final catalytic compositions generally have a B.E.T. specific surface of between 25 ml/g and 200 ml/g and preferably between 50 and 150 m$^2$/g. Good results for the oxychlorination of ethylene have been obtained with catalytic compositions having a B.E.T. specific surface of from 80 to 140 m$^2$/g.

The catalytic compositions according to the invention are particularly advantageous in an oxychlorination process in which the catalyst is in the form of a fluidized bed. They may, nevertheless, also be used in an oxychlorination process performed with a catalyst located in a fixed bed, provided that the catalyst particles are in a suitable form, for example in the form of granules a few mm in diameter. The catalytic compositions according to the invention are suitable for oxychlorination processes in air or in oxygen. They are particularly well suited to the process in oxygen, using pure oxygen or an oxygen/nitrogen mixture which is richer in oxygen than air.

The catalytic compositions according to the invention are most particularly suitable for a process for the oxychlorination in oxygen of ethylene into 1,2-dichloroethane in which the catalyst is in the form of a fluidized bed. Such a process making use of a catalytic composition according to the invention is particularly preferred.

When the process is performed with a catalyst located in a fluidized bed, the temperature at which the oxychlorination reaction is carried out is usually between 200° and 300° C. This temperature is preferably between 220° and 280° C. Good results have been obtained at a temperature in the region of 230°–270° C.

The pressure at which the oxychlorination reaction is carried out is not critical per se. Usually, the process is performed with pressures of between 0.1 and 1 MPa and preferably with pressures of between 0.1 and 0.8 MPa. The rate of fluidization of the catalytic compositions is not critical per se and depends essentially on the particle size of the catalyst and on the size of the apparatus. The process is generally performed with rates of between 5 and 100 cm/s. Finally, the ratio of the reactants used is the same as that generally used in the prior processes. Usually, the process is performed with a slight excess of ethylene relative to the stoichiometric amount needed to react with the HCl used. However, the catalytic compositions of the invention make it equally possible to work with large excesses of ethylene or amounts in the region of the stoichiometry, or even in an excess of HCl.

The invention is more fully illustrated by the examples which follow. The examples labelled (c) relate to examples given for comparison.

EXAMPLES 1 TO 6

A catalyst according to the invention was prepared from a gamma alumina having a specific surface of 186 m$^2$/g, a pore volume of 0.38 cm$^3$/g, a specific gravity (measured by free flow) of 0.75 kg/dm$^3$ and a mean particle diameter of 50 μm. To about 800 g of this alumina was added an aqueous impregnation solution comprising, in the dissolved state, CuCl$_2$.2H$_2$O, MgCl$_2$.6H$_2$O and CsCl in appropriate amounts in order to obtain, after drying at 150° C., about 1 kg of catalyst having, calculated as metal relative to the total weight of the catalyst, a copper content of 60 g/kg, a magnesium content of 17 g/kg and a caesium content of 1 g/kg. The proportion of the various metals Cu:Mg:Cs expressed as an atomic ratio is 1:0.74:0,008.

A second catalyst according to the invention and four other catalysts, consisting solely of copper chloride and of caesium chloride on alumina or of copper chloride and of magnesium chloride on alumina, were prepared according to the same procedure. The metal contents in these various catalysts are presented in Table I.

These 6 catalysts were tested in the oxychlorination of ethylene in a fluid bed micro-pilot reactor, containing 280 cm$^3$ of catalyst. The catalyst is fluidized using the reactant gases which are introduced via the bottom through a sintered metal filter. The operating conditions in which the tests were performed are as follows:

2C$_2$H$_4$/HCl ratio=1.04 mol/mol
4O$_2$/HCl ratio variable, so as to maintain 1% volume of O$_2$ in the tail gases.
Flow rate of the gases: 12.5 cm/s (relative to the empty reactor at the test pressure and temperature) Temperature: 255° C.
Pressure: 0.6 MPa
Residence time: 5 s.

The reaction products leaving the reactor were depressurized to atmospheric pressure by a pressure control valve on the reactor and were cooled in a trap maintained at −20° C. The uncondensed gases were washed in a water scrubber before sweeping over a sampling bulb. The products formed were determined by chromatographic analyses of the liquid and gaseous products collected and from acidimetric titration of the aqueous solution collected at the foot of the scrubber. The yield of 1,2-dichloroethane (molar ratio between the DQEa formed and the HCl used) and the selectivity for DCEa (molar ratio between the DCEa formed and the ethylene converted) are presented in Table I.

The deposition of soiling material caused by the various catalysts was measured in a micro-pilot reactor similar to the reactor described above but also fitted with a finger-shaped tube descending vertically into the fluid bed. This finger tube is composed of a double wall in which circulates an oil maintained at a temperature below the temperature at which the reaction is carried out. The deposition of soiling material is determined visually by examining the outer surface of this finger tube after the reactor has been operating for 20 hours under the following conditions:

2C$_2$H$_4$/HCl ratio=1.07 mol/mol
4O$_2$/HCl ratio=1.12
Flow rate of the gases: 2.5 cm/s
Temperature in the fluid bed: 270° C.
Temperature at the outer surface of the finger tube: 180° C.
Pressure: 0.7 MPa
Residence time: 12 s.

Under these conditions, the results obtained reflect the behavior of the catalysts which is observed after operation for a few months in an industrial reactor. A numerical value is given to the catalysts, according to the appearance of the soiling material and to the location at which it appears on the outer surface of the finger tube. A diagram of the finger tube (1) descending into the fluid bed (2) is given in the single figure. The tube contains 4 distinct regions: a conical tip (3), a cylindrical surface (4) descending into the fluid bed (2), an interface (5) located just above the fluid bed and a cylindrical surface (6) which is out of the fluid bed, above the interface (5). The presence of a film, that is to say of a fine adhering coating which contains no catalyst particles, at the tip (3) or at the surface (4) descending into the fluid bed is worth 1 point. The presence of a crust, that is to say of a thicker deposit containing catalyst particles adhering to the surface of the tube, is worth 2 points at the tip (3) and at the surface (4) and 1 point at the interface (5). On that region of the surface (6) which is out of the bed, only the presence of aggregates of catalyst particles was sometimes observed and is counted as 1 point. The presence of non-adherent catalyst particles on any part of the surface of the tube is not taken into account. Finally, poor fluidization of the catalyst resulting in the setting thereof counts as 6 points. A value of 0 will thus be given to a catalyst which does not give rise to any deposition of soiling material during the test, whereas a catalyst which gives rise to a considerable appearance of soiling material, demonstrated, for example, by the presence of crusts at the tip (3) (2 points), at the surface (4) (2 points) and at the interface (1 point) will be given a value of 5.

The results obtained are presented in Table I.

It emerges clearly from the comparison between Examples 1 and 2 according to the invention and Comparative Examples 3(c) to 6(c) that the simultaneous presence of magnesium chloride and caesium chloride in the catalytic composition enables good chemical performance (yield and selectivity) to be obtained without causing the deposition of soiling material, which is not the case when only one of these two chlorides is present in the catalytic composition, even at a higher content.

EXAMPLES 7 TO 15

The catalysts used in Examples 7 to 15 were prepared in the same way as the catalysts of Examples 1 to 6, starting with the same alumina impregnated with an aqueous solution containing CuCl$_2$.2H$_2$O, MgCl$_2$.6H$_2$O and CsCl, KCl, LiCl or NaCl in appropriate amounts and proportions.

The various catalysts were tested in the oxychlorination of ethylene in the fluid bed micro-pilot reactor used in Examples 1 to 6, under the following operating conditions:

Volume of catalyst: 225 cm$^3$
2C$_2$H$_4$/HCl ratio=1.07 mol/mol
4O$_2$/HCl ratio: 1.35 mol/mol
Flow rate of the gases: 10 cm/s (relative to the empty reactor at the test pressure and temperature) Temperature: 260° C.
Pressure: 0.6 MPa
Residence time: 5 s.

The deposition of soiling material was measured according to the same procedure as that used in the tests to Examples 1 to 6.

Table II below summarizes the compositions of the various catalysts tested, the results obtained for the oxychlorination of ethylene and the soiling material deposition measurements.

The catalytic compositions of the Comparative Examples 10 to 15 give a good yield of 1,2-dichloroethane relative to the HCl and a good selectivity for ethylene into 1,2-dichloroethane, but cause deposition of soiling material on the surface of the finger tube. In contrast, Examples 7 to 9 demonstrate that the compositions according to the invention do not cause any deposition of soiling material, while at the same time providing a very high selectivity and yield of 1,2-dichloroethane.

EXAMPLE 16

A catalyst containing copper, magnesium, caesium and potassium was prepared in a similar manner to the catalysts used in Tests 1 to 15. This catalyst contained 59 g of copper, 17 g of magnesium, 1.7 g of caesium and 3 g of potassium per kilo. It was tested under the same conditions as those of Examples 1 to 6.

Under these conditions, this composition causes no deposition of soiling material (value:zero) and provides a remarkably high selectivity for DCEa relative to the ethylene converted (98.4 mol %), while at the same time providing an acceptable yield of 1,2-dichloroethane relative to the HCl (97 mol %).

TABLE I

| | Composition | | | | | Yield of DCEa relative to the HCl | Selectivity for DCEa relative to the ethylene converted | Deposition of soiling material |
|---|---|---|---|---|---|---|---|---|
| | weight content (g/kg) | | | Atomic proportions | | | | |
| Ex. No. | Cu | Mg | Cs | Cu | Mg | Cs | (mol %) | (mol %) | (see text) |
| 1 | 60 | 17 | 1 | 1 | 0.74 | 0.008 | 98.3 | 96.7 | 0 |
| 2 | 62 | 18 | 2.6 | 1 | 0.76 | 0.020 | 98.6 | 97.7 | 0 |
| 3(c) | 60 | 17 | — | 1 | 0.74 | — | 98.2 | 96.8 | 3 |
| 4(c) | 60 | 24 | — | 1 | 1.05 | — | 96.5 | 98.1 | 3 |
| 5(c) | 60 | — | 1 | 1 | — | 0.008 | 97.7 | 94.2 | 10 |
| 6(c) | 60 | — | 3 | 1 | — | 0.024 | 97.7 | 94.6 | 10 |

TABLE II

| | Composition | | | | | | Yield of DCEa relative to the HCl | Selectivity for DCEa relative to the ethylene converted | Deposition of soiling material |
|---|---|---|---|---|---|---|---|---|---|
| | weight content (g/kg) | | | Atomic proportions | | | | | |
| Ex. No. | Cu | Mg | Alk | Cu | Mg | Alk | (mol %) | (mol %) | (see text) |
| 7 | 60 | 17 | 1 Cs | 1 | 0.74 | 0.008 Cs | 98.3 | 96.2 | 0 |
| 8 | 60 | 17 | 4.6 Cs | 1 | 0.74 | 0.04 Cs | 97.8 | 97.3 | 0 |
| 9 | 60 | 17 | 8.7 Cs | 1 | 0.74 | 0.07 Cs | 97.2 | 97.6 | 0 |
| 10(c) | 60 | 17 | 2.1 Li | 1 | 0.74 | 0.33 Li | 97.5 | 94.9 | 3 |
| 11(c) | 56 | 17 | 3.1 Li | 1 | 0.79 | 0.51 Li | 98.2 | 96.7 | 3 |
| 12(c) | 60 | 18 | 2.1 Na | 1 | 0.80 | 0.10 Na | 97.9 | 94.4 | 1 |
| 13(c) | 60 | 17 | 4.4 Na | 1 | 0.74 | 0.21 Na | 98.2 | 96.0 | 4 |
| 14(c) | 58 | 17 | 11K | 1 | 0.77 | 0.31K | 98.2 | 96.8 | 1 |
| 15(c) | 60 | 17 | 17K | 1 | 0.74 | 0.47K | 97.9 | 97.2 | 1 |

What is claimed is:

1. A catalytic composition consisting essentially of copper chloride, magnesium chloride and an alkali metal chloride deposited on an alumina, wherein the alkali metal is caesium or a mixture of caesium and potassium.

2. The catalytic composition according to claim 1, containing from 30 to 90 g of copper, from 10 to 30 g of magnesium and from 0.1 to 10 g of caesium, expressed as metal, per kilo of catalytic composition.

3. The catalytic composition according to claim 1, containing from 40 to 80 g of copper, from 12 to 25 g of magnesium and from 0.5 to 9 g of caesium, expressed as metal, per kilo of catalytic composition.

4. The catalytic composition according to claim 1, in which the Cs/Cu atomic ratio is from 0.003 to 0.10.

5. The catalytic composition according to claim 1, in which the Cu:Mg:Cs atomic ratios are 1:0.5–1.0 :0.005–0.05.

6. The catalytic composition according to claim 1, wherein the alkali metal is a mixture of caesium and potassium.

7. The catalytic composition according to claim 6, in which the K/Cu atomic ratio is from 0.01 to 0.30.

8. The catalytic composition according to claim 1, in which the alumina has a specific surface, measured according to the B.E.T. method, of between 50 m$^2$/g and 250 m$^2$/g.

9. A process for the oxychlorination of ethylene into 1,2-dichloroethane by reaction with hydrogen chloride in the presence of air or oxygen, characterized in that the oxychlorination reaction is catalysed by a catalytic composition according to claim 1.

10. The oxychlorination process according to claim 9, in which the catalytic composition is in the form of a fluidized bed.

11. The oxychlorination process according to claim 9, in which the oxygen used is either in pure form or in the form of an oxygen and nitrogen mixture which is richer in oxygen than air.

12. A catalytic composition consisting of copper chloride, magnesium chloride and an alkali metal chloride deposited on an alumina, wherein the alkali metal is caesium or a mixture of caesium and potassium.

* * * * *